US010398886B2

(12) United States Patent
Myers

(10) Patent No.: US 10,398,886 B2
(45) Date of Patent: Sep. 3, 2019

(54) ASPIRATION APPARATUS AND METHOD OF USING THE SAME

(71) Applicant: Kristi A. Myers, Port Orange, FL (US)

(72) Inventor: Kristi A. Myers, Port Orange, FL (US)

(73) Assignee: Myers Devices LLC, Daytona Beach, FL (US)

( * ) Notice: Subject to any disclaimer, the term of this patent is extended or adjusted under 35 U.S.C. 154(b) by 0 days.

(21) Appl. No.: 15/756,964

(22) PCT Filed: Sep. 19, 2016

(86) PCT No.: PCT/US2016/052532
§ 371 (c)(1),
(2) Date: Mar. 1, 2018

(87) PCT Pub. No.: WO2017/058556
PCT Pub. Date: Apr. 6, 2017

(65) Prior Publication Data
US 2018/0256877 A1     Sep. 13, 2018

Related U.S. Application Data

(60) Provisional application No. 62/236,555, filed on Oct. 2, 2015.

(51) Int. Cl.
*A61M 1/00*     (2006.01)
*A61M 39/08*     (2006.01)

(52) U.S. Cl.
CPC ............ *A61M 39/08* (2013.01); *A61M 1/008* (2013.01); *A61M 2209/06* (2013.01); *A61M 2209/08* (2013.01)

(58) Field of Classification Search
CPC ............ A61M 39/08; A61M 2039/087; A61M 1/008; A61M 2209/06; A61M 2209/08;
(Continued)

(56) References Cited

U.S. PATENT DOCUMENTS 5,224,679 A    7/1993   Code
5,471,706 A    12/1995   Wallock et al.
(Continued)

FOREIGN PATENT DOCUMENTS

WO       9728067       8/1997

OTHER PUBLICATIONS

Medstrap Holster: http://www.futuremedinc.net/portfolio/medstrap-holster/.

*Primary Examiner* — Steven A. Reynolds
*Assistant Examiner* — Javier A Pagan
(74) *Attorney, Agent, or Firm* — GFD Patents LLC; Gerald F. Dudding

(57) ABSTRACT

Leak-resistant Kits for releasably retaining a medical suction tube, e.g. a Yankauer Suction Instrument used to collect biological fluids during a medical procedure and method of use is described. The leak-resistant Kit comprises an apparatus that includes a leak proof solid bottom portion, a hollow cavity reservoir, and a top portion with a leak resistant flexible retaining disk. The flexible retaining disk functions to releasably hold, releasably retain or releasably restrict the undesired movement of a Yankauer Suction Instrument after being inserted into the disk. In addition, the flexible retaining disk functions as a splash guard for preventing biological fluids from being ejected from the reservoir. The leak-resistant Kit allows the user the ability to use one hand to manipulate a Yankauer Suction Instrument. Additionally, the apparatus fits onto a movable bracket that can also be used with one hand.

9 Claims, 13 Drawing Sheets

(58) Field of Classification Search
CPC ...... A61M 2209/082; A61M 2209/084; A61M 2209/086; A61M 2209/088; A61M 2209/10
See application file for complete search history.

(56) References Cited

U.S. PATENT DOCUMENTS

| | | | |
|---|---|---|---|
| 5,871,189 A | 2/1999 | Hoftman | |
| 6,077,074 A * | 6/2000 | Homra | A61M 1/0039 433/77 |
| 6,257,888 B1 | 7/2001 | Barham | |
| 7,913,959 B2 | 3/2011 | White et al. | |
| 7,967,225 B1 | 6/2011 | Schulz | |
| 8,302,776 B2 | 11/2012 | Lien | |
| 8,663,173 B2 | 3/2014 | Wheeler et al. | |
| 8,833,556 B2 | 9/2014 | Wright | |
| 8,978,907 B2 | 3/2015 | Greenberg | |
| 9,044,853 B2 | 6/2015 | Phui | |
| 9,222,324 B2 | 12/2015 | Russel | |
| 2007/0088330 A1 | 4/2007 | House | |
| 2007/0094770 A1 | 5/2007 | Ciesinski et al. | |
| 2014/0319375 A1* | 10/2014 | Nelson | A61L 2/025 250/455.11 |
| 2015/0128535 A1 | 5/2015 | McInnis | |
| 2015/0218786 A1* | 8/2015 | Cullen | A46B 15/00 4/628 |
| 2015/0320419 A1 | 11/2015 | Gorek et al. | |
| 2016/0015214 A1 | 1/2016 | Laegdsgaard | |

* cited by examiner

550

560 displacing a top surface 40, 240, or a leak-proof seal 134 of a fixed retaining disk 13, a displacable retaining disk 75 or a leak proof seal 134 of a displacable member 1333 of Kit 1, Kit 2, or Kit 3, respectively, from a rim 15 of the leak-proof container 137, e.g., a retaining holster 5 lengthwise along a hollow cavity 132 of Kit 1, Kit 2, or Kit 3, respectively.

FIG. 20

ASPIRATION APPARATUS AND METHOD OF USING THE SAME

I. FIELD OF THE INVENTION

The present invention relates generally to devices used to store, releasably hold, releasably retain or releasably restrict the undesired movement of a suction instrument, most commonly in a location where it can be easily withdrawn for immediate use, and more specifically to store, releasably hold, releasably retain or releasably restrict the undesired movement of a Yankauer Suction Instrument before, during, or after use in a medical procedure.

II. BACKGROUND

U.S. Pat. No. 8,833,556 B2 to Wright shows a suction tip holster insert; more specifically, it discloses a cleaning and storage system for an aspiration instrument. This system consists of a removable and disposable insert, which must be folded down to stay in place. It also fashions a ledge inside the holster to support the tip of the suction tube off the base of the unit to allow for fluids and secretions to drip into the base. With this holster the suction tube is not reliably held within the disposable insert and if the base unit is oriented any way other than vertically, the suction tube can fall out and become contaminated as well as contaminate anything it touches. This holster requires additional set up time to place the disposable insert into the holster and fold down the edges. This can be detrimental in the case of an emergency, when time matters. The means for attaching the holster to various objects, such as a bed rail, ventilator, hospital stand, or wall, requires two hands to attach a clip, tie-straps, or adhesive strips, which again, takes extra time for set up, and in addition, the holster can not be easily moved to another location if needed, which is often the case in real practice. The feature of having a ledge to hold the suction tip above the base of the insert is not warranted because in real practice, most residual secretions are suctioned away from the tip and into the suction tubing, leaving little to no residual secretions to actually drip from the end of the tip.

U.S. Pat. No. 5,224,679 to Code shows a holster for securing a contamination-barrier sac for an instrument, specifically intake nozzles of medical and dental operating room suction equipment. It shows that normally such intake nozzles are sealed in a sterile bubble wrap leading to an opportune time to utilize this existing wrap as a contaminating-barrier sac, but states that alternatively, a disposable sterilizable liner may be used. This holster has an opening at both the upper and lower ends with a clip on the inside of each end to attach and hold either type of contamination barrier sac in place. This method of containing the sac requires the user to use both hands to clip the sac properly into each clip, which is time consuming. More importantly, it does not offer a way to prevent the sac from being punctured, especially through the bottom end of the sac, when the suction tube tip is placed in and out of the sac, as it offers no solid bottom surface. The intake nozzle can puncture through the bottom of the sac if there is nothing to support it. The clips themselves may also puncture the sac, leaving the suction tip exposed to the inside of the holster, thereby contaminating the inside of the holster as well as contaminating the intake nozzle. The device itself offers no retaining capability for the suction tube to reliably stay inside the holster and it is impossible to use with one hand.

U.S. Pat. application Ser. No. 2006/0192064 A1 to White, U.S. Pat. No. 7,377,780 B2 to White, 7,422,421 B2 to White and U.S. Pat. No. 7,913,959 B2 to White show a medical/dental suction nozzle holster with varying features. The primary characteristic of White's holster is that it may be oriented in three distinct operating positions with respect to the floor of the room in which it is located. Although White's holster may be oriented in three different operating positions, White's holster's design does not prevent the suction nozzle from falling out of the open end of the holster if the open end of the holster is pitched downward. White's holster also requires the use of both hands to mount the holster to an object and to change it into any of the three separation ribs that it houses, taking the users attention away from patient care. This type of mount can only be attached to a rail and can not be attached to other items such as IV poles, work carts, anesthesia machines, or nearby medical equipment which would prevent it from being used exactly where it may need to be located. This device also offers no way to reliably retain the suction nozzle from falling out of the holster.

One objective of the present invention is to provide a kit for storing, releasably holding, releasably retaining or releasably restricting the undesired movement of a medical suction tube, e.g. Yankauer Suction Instrument before, during, or after use in a medical procedure.

A second objective is to provide a method for storing, releasably holding, releasably retaining or releasably restricting undesired movement of a medical suction tube, e.g. Yankauer Suction Instrument before use, during use, or after use in a medical procedure in which the medical suction tube is used to collect biological fluids during the medical procedure.

A third objective is to store, releasably hold, releasably retain or releasably restrict undesired movement of a medical suction tube, e.g., Yankauer Suction Instrument before use, during use, or after use in a medical procedure in which the medical suction tube, e.g., Yankauer Suction Instrument in a location where it can be parked or withdrawn for immediate use by an operator using only one hand.

Therefore, there is a need for storing, releasably holding, releasably retaining or releasably restricting the undesired movement of an instrument before, during, or after use in a medical procedure.

SUMMARY OF THE INVENTION

A first aspect of the present invention provides a kit for releasably retaining a medical suction tube before being used or after being used to collect biological fluids during a medical procedure. The kit is comprised of a leak-resistant container with a rim end, a leak-proof opposing bottom end, with a reservoir between them for containing drippings of the biological fluids from the suction tube, and a recessed lid. The recessed lid has a coupling, a peripheral edge of which overlaps the rim end of the container, so that the rim end is covered by the peripheral portion, allowing the rim end and peripheral portion to fit into a groove formed by the peripheral edge overlapping the rim end. A retaining disk is peripherally coupled to a distal suction end of a recessed portion, such that there is a measurable length $L_1$ separating the rim end from a top surface of the retaining disk. The retaining disk has slits that radiate from a center, where the slits divide the retaining disk into a plurality of flexible arcuate flaps. At least one of the plurality of flexible arcuate flaps flex toward the bottom end when the suction end of the suction tube contacts the plurality of flexible arcuate flaps during insertion of said suction end of the suction tube into the hollow cavity. This forms a central aperture through the center of the recessed lid. The flexible arcuate flaps and central aperture of the recessed lid are thus operative in combination with said suction tube as a splash guard for preventing biological fluids from being ejected from a reservoir of the hollow cavity between the recessed lid and the bottom end, and for releasably retaining the suction end of the suction tube in the reservoir after insertion of the suction end through the central aperture.

A second aspect of the present invention provides a kit for releasably retaining a medical suction tube before being used or after being used to collect biological fluids during a medical procedure. The kit contains a leak-resistant container having a rim end and an opposing leak-proof bottom end. Only the rim end is open, and opens into a hollow cavity. The kit also contains a displaceable retaining disk having a central aperture for insertion of the medical suction tube into the hollow cavity. The hollow cavity has slits that radiate from a center, the slits dividing the retaining disk into a plurality of flexible arcuate flaps. At least one of the plurality of flexible arcuate flaps flexes towards the bottom end when the suction end of the suction tube contacts the plurality of flexible arcuate flaps during insertion of the suction end of the suction tube into the hollow cavity. This forms a central aperture through the center of the displaceable retaining disk. The flexible arcuate flaps and central aperture of the displaceable retaining disk are operative in combination with the suction tube as a splash guard for preventing biological fluids from being ejected from the reservoir of the hollow cavity that is between the displaceable retaining disk and the bottom end and for releasably retaining the suction end of the suction tube in the reservoir after insertion of the suction end through the central aperture.

A third aspect of the present invention provides a method of releasably retaining a medical suction tube after being used to collect biological fluids during a medical procedure. The method consists of: Providing either kit for retaining said suction tube after insertion of the suction end of the suction tube through the central aperture of claim 1 or claim 3, and then releasably inserting the medical suction tube into the central aperture.

BRIEF DESCRIPTION OF THE DRAWINGS

The features of the invention are set forth in the appended claims. The invention itself, however, will be best understood by reference to the following detailed description of an illustrative embodiment when read in conjunction with the accompanying drawings, wherein:

FIG. 20 depicts a flow diagram of a method 550 for positioning the fixed displacement retaining disk 13 or the displaceable retaining disk 75 or the displaceable member 1333 along a length L1, L2, or L3 of the hollow cavity 132, in accordance with embodiments of the present invention.

DETAILED DESCRIPTION OF THE EMBODIMENTS OF THE INVENTION

Figure 1:
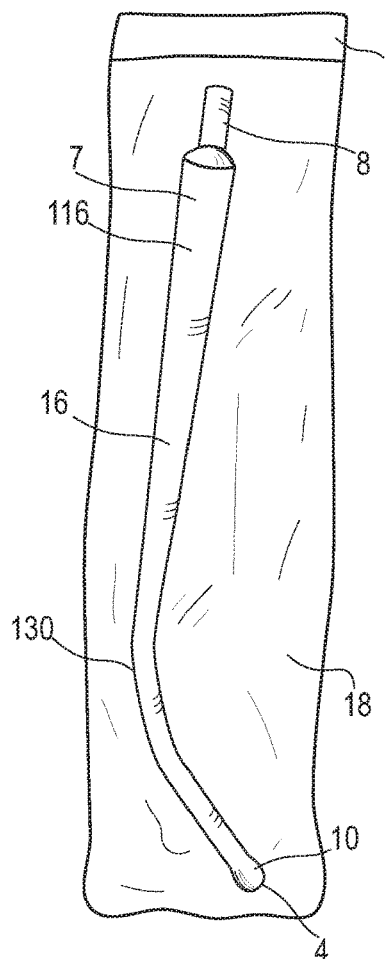
FIG. 1 depicts a side elevation view of a medical suction tube, e.g., Yankauer Suction Instrument in its original, sterile package, in accordance with embodiments of the present invention.

Definitions:

As used herein, unless defined otherwise, the term "distal suction end", in reference to a medical suction tube 16, e.g., Yankauer Suction Instrument is defined as the suction end 10 of the medical suction tube 16, e.g., Yankauer Suction Instrument that applies suction before, during, or after use in a medical procedure.

As used herein, unless defined otherwise, the term "proximal end", in reference to a medical suction tube 16, e.g., Yankauer Suction Instrument is defined as the end 10 of the medical suction tube 16, e.g., Yankauer Suction Instrument that is coupled to a source of suction before, during, or after use in a medical procedure.

As used herein, unless defined otherwise, the singular forms "a", "an", and "the" include plural referents unless the context clearly dictates otherwise. Thus, for example, reference to "at least one flexible flap" includes a plurality of such flexible flaps, and so forth.

As used herein, unless defined otherwise, the term "frustoconical" means having a shape of a frustum of a cone.

As used herein, unless defined otherwise, the term "annulus" means a ring-shaped part, figure, or space. In the present teachings, annulus refers to the shape of the fixed displacement retaining disk 13 being a ring between the overlapping extension 110 of the recessed lid 50 and the central aperture 60 or tube 160 of the recessed lid 50. An example of an annulus is the area between two concentric circles.

As used herein, unless defined otherwise, the term "splash guard" 133 means a penetrable barrier, e.g., the retaining disks 13, 75, and displaceable retaining member 1333, covering the retaining holster 5 of leak-resistant Kits 1, 2, or 3, such that the retaining holster 5 becomes leak-resistant. The splash guard 133 has slits 23 radiating from a center 60 or a central aperture 70 defining flexible arcuate flaps 65, operative in combination with a medical suction tube 16, e.g., Yankauer Suction Instrument being inserted into a central aperture 70.

As used herein, unless defined otherwise, the term "releasable seal," "releasably sealing," or "releasably sealed" in reference to releasable seals 119, 129, and 134 is defined as forming or breaking or cleaving or severing or re-forming a mechanical and physical coupling, e.g. the "releasable seal", between the inner wall 85 of the retaining holster 5 and the retaining disks 13, 75, or between the inner wall 85 of the retaining holster 5 and the displaceable retaining member 1333. The retaining disks 13, 75, and the displaceable retaining member 1333 are releasably sealed to the inner wall 85 of the retaining holster 5, such that the Kit 2, 3 remain leak-resistant when the displaceable retaining disk 75 or the displaceable retaining member 1333 slides corresponding to $L_2$ or $L_3$, respectively.

As used herein, unless defined otherwise, the term "leak resistant" in reference to the leak-resistant Kits 1, 2, or 3, specifically the holster 5 of the Kits 1, 2, or 3 refers to a shielding function of the "splash guard" 133 whereby biological fluids 3 in the reservoir 14 of a medical holster 5 are partially blocked from being ejected from the reservoir 14 of the hollow cavity 132 that is between the recessed lid 50 and the bottom end 135, when the holster 5 of the Kit 1, Kit 2, Kit 3 are upended or laid on their side before, during, or after use in a medical procedure because the splash guard 133 comprises overlapping flexible arcuate flaps 65, defined by slits 23 radiating from a center 60 or a central aperture 70, overlap. The biological fluids 3 in the reservoir 14 of a medical holster 5 are partially blocked from being ejected from the reservoir 14 of the hollow cavity 132 that is between the recessed lid 50 and the bottom end 135, when the holster 5 of the Kit 1, Kit 2, Kit 3 are upended or laid on their side before, during, or after use in a medical procedure because the flexible arcuate flaps 65 overlap the slits 23, preventing ejection of the biological fluids 3. In addition, the splash guard 133 and the releasable seals 119, 129, and 134 are leak-resistant because the splash guard 133 is made from a water proof material selected from the group consisting of elastomeric plastic, elastomeric silicone, and rubber. Therefore the Kits 1, 2, or 3 having the leak-resistant splash guards 133 are also leak-resistant because the Kits 1, 2, or 3 comprise the leak-resistant splash guards 133.

As used herein, unless otherwise defined, the term "propped up" is used to describe a stabilized orientation of the medical suction tube 16, e.g., the Yankauer Suction Instrument during storage in the retaining holster 5, yielding increased stabilization of the medical suction tube 16, e.g., the Yankauer Suction Instrument during storage, releasably holding, releasably retaining, or releasably restricting from undesired movement.

In Kit 1 having been constructed such that the fixed displacement disk 13 has fixed displacement, designated by $L_1$, resistance to displacement of the flexible arcuate flaps 65 when the medical suction instrument 16 is inserted in the central aperture 70 of the fixed displacement retaining disk 13, point of contact 137 of curved portion 130 of the tube 16 with contact 138 of the inner wall 85 of the retaining holster 5 and the contact of the bulbous tip 4 with the bottom end 135 of the retaining holster 5 exert frictional forces on the tube 16, such that it is propped up by these frictional forces exerted on the tube 16. Said propping up of the tube 16 results in increased stabilization of the medical suction tube 16, e.g., the Yankauer Suction Instrument during storage, releasably holding, releasably retaining, or releasably restricting from undesired movement.

In Kit 2, having been constructed such that the displaceable disk 75 has variable displacement, designated by $L_2$, resistance to displacement of the flexible arcuate flaps 65 when the medical suction instrument 16 is inserted in the central aperture 70 of the displaceable retaining disk 75, point of contact 137 of curved portion 130 of the tube 16 with contact 138 of the inner wall 85 of the retaining holster 5 and the contact of the bulbous tip 4 with the bottom end 135 of the retaining holster 5 exert frictional forces on the tube 16, such that it is propped up by these frictional forces exerted on the tube 16. Said propping up of the tube 16 results in increased stabilization of the medical suction tube 16, e.g., the Yankauer Suction Instrument during storage, releasably holding, releasably retaining, or releasably restricting from undesired movement.

In Kit 3, having been constructed such that the displaceable retaining member 1333 has variable displacement, designated by $L_3$, resistance to displacement of the grippers 123 when the medical suction instrument 16 is inserted in the central aperture 1230 of the displaceable retaining member 1333, point of contact 137 of curved portion 130 of the tube 16 with contact 138 of the inner wall 85 of the retaining holster 5 and the contact of the bulbous tip 4 with the bottom end 135 of the retaining holster 5 exert frictional forces on the tube 16, such that it is propped up by these frictional forces exerted on the tube 16. Said propping up of the tube 16 results in increased stabilization of the medical suction tube 16, e.g., the Yankauer Suction Instrument during storage, releasably holding, releasably retaining, or releasably restricting from undesired movement.

FIG. 1 depicts a side elevation view of a medical suction tube 16, e.g., a Yankauer Suction Instrument in its original, sterile package 18. The medical suction tube 16 may be typically embodied as a firm plastic suction tube engineered to allow effective suctioning without damaging surrounding tissue. It may have a bulbous tip 4 on its suction, or distal suction end 10, that may be placed, for example, in a patient's mouth to suction oropharyngeal secretions.

Figure 2:
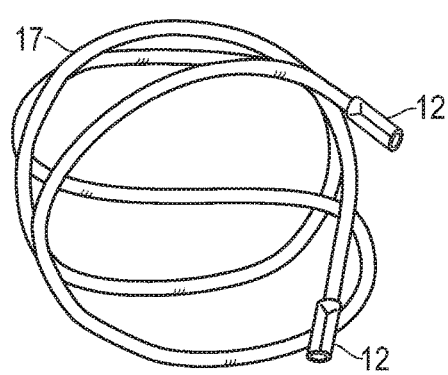
FIG. 2 depicts a side elevation view of typical suction tubing, in accordance with embodiments of the present invention.

FIG. 2 depicts a side elevation view of typical suction tubing 17 having ends 12.

Figure 3A:
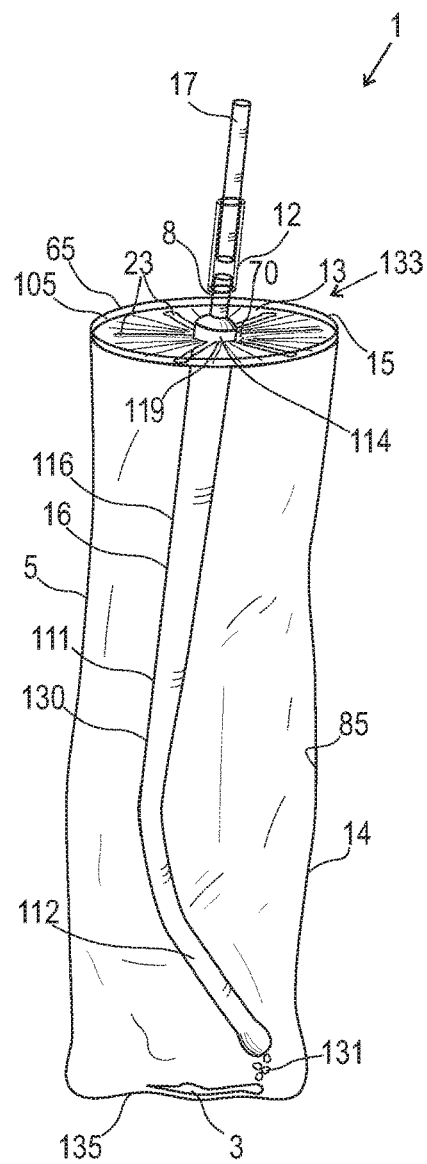
FIGS. 3A-3B depicts a side elevation view of leak-resistant Kit 1, coupled to the suction tubing depicted in FIG. 2, in accordance with embodiments of the present invention.
Figure 3B:
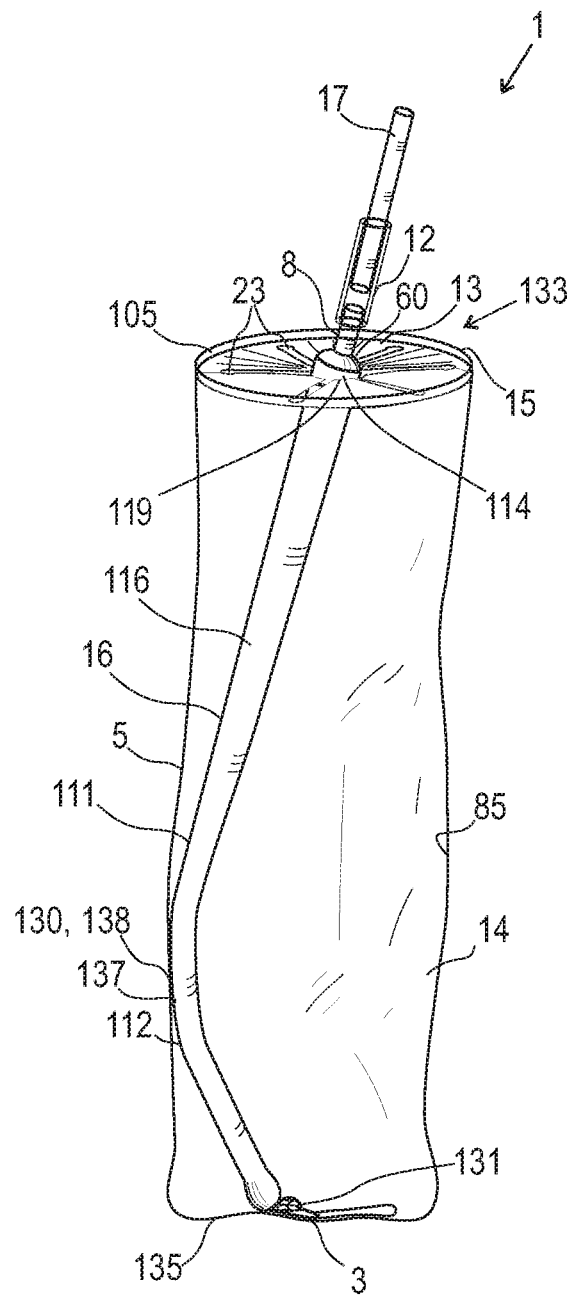
Figure 4:
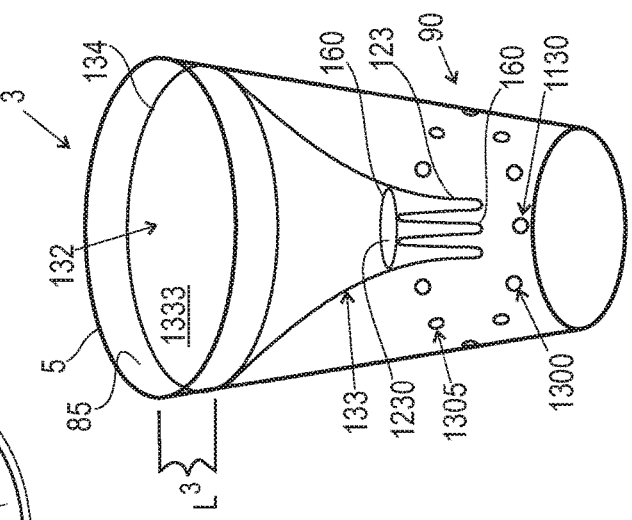
FIG. 4 depicts a front elevation view of the leak-resistant Kit 1, in accordance with embodiments of the present invention.

FIGS. 3A-3B depict a side elevation view of a combination or leak-resistant Kit 1, comprising the medical suction tube 16, depicted in FIG. 1, e.g. a Yaukauer Tube, after it has been inserted into a retaining holster 5. The medical suction tube 16 has a bulbous handle section 116 at the proximal end 7. The medical suction tube 16 has a coupling 8 on its proximal end 7, that may be operably coupled to a suction source, e.g., a vacuum pump or in-hospital vacuum supply (not shown) via suction tubing 17 of various lengths. A suction connection section 114 and a connection end 8 at the proximal end 7 thereof are for connection to a suction source (not shown).

The medical suction tube 16, e.g., Yankauer Suction Instrument terminates at a suction tip section 112 and a suction tip 4 at the distal suction end 10 thereof. Usually the biological fluids 3 that are suctioned out of the patient during the medical procedure are trapped in a waste collection canister (not shown) which prevents the waste biological fluids 3 from being drawn into the suction source. The secretions may be drawn from the patient's mouth through the medical suction tube 16, e.g., the Yankauer Suction Instrument and then through the suction tubing 17, where it may continue to be drawn into the waste collection canister (not shown).

Referring to FIGS. 1 and 3A-3B a portion of the medical suction tube 16, e.g., Yankauer Suction Instrument forms a curved portion 130 approximately 50% along its length. The curved portion 130 is a continuous curve between an essentially straight portion 111 that is an extension of the suction connection section 114 and a suction tip section 112.

The medical suction tube 16 in FIGS. 1 and 3 may be of different length and diameters, depending on application. In one embodiment, the medical suction tube 16, e.g., a Yankauer Suction Instrument may be 20-30 cm in length, and 1-2 cm in diameter. The diameter of the tube 16 may taper, or gradually decrease from the proximal end 7 to the bulbous tip 4 on its suction, or distal suction end 10.

In FIGS. 3A and 3B, Kit 1 having been constructed such that the fixed displacement disk 13 has fixed displacement, designated by $L_1$, resistance to displacement of the flexible arcuate flaps 65 when the medical suction instrument 16 is inserted in the central aperture 70 of the fixed displacement retaining disk 13, point of contact 137 of curved portion 130 of the tube 16 with contact 138 of the inner wall 85 of the retaining holster 5 and the contact of the bulbous tip 4 with the bottom end 135 of the retaining holster 5 exert frictional forces on the tube 16, such that it is propped up by these frictional forces exerted on the tube 16. Said propping up of the tube 16 results in increased stabilization of the medical suction tube 16, e.g., the Yankauer Suction Instrument during storage, releasably holding, releasably retaining, or releasably restricting from undesired movement.

Figure 6A:
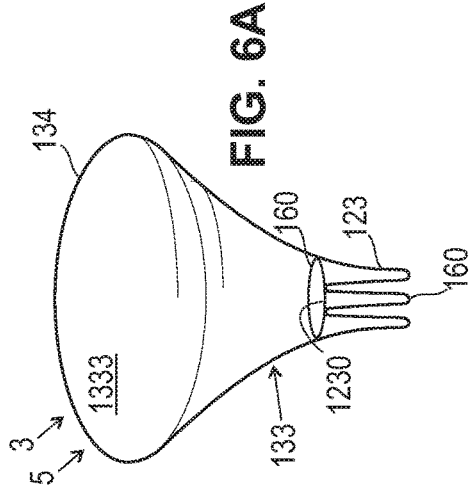
FIG. 6A depict leak-resistant Kit 3, having a side elevation view of a displaceable retaining member 1333 having elongated grippers 123 extending from an annulus 160, in accordance with embodiments of the present invention.
Figure 6B:
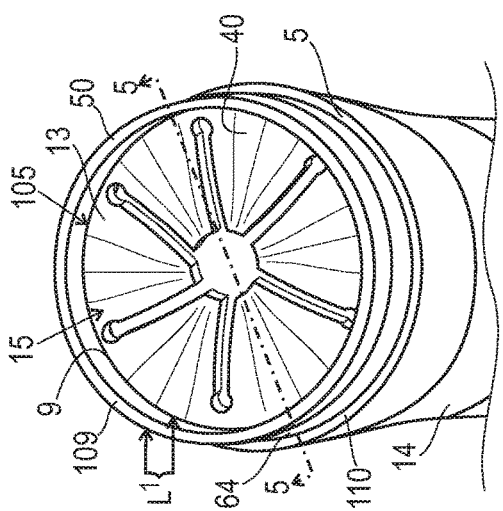
FIG. 6B depicts leak-resistant Kit 3, after opposing Light Emitting Diode (LED) arrays have been arranged circumferentially along the inner wall of the retaining holster, in accordance with embodiments of the present invention.
Figure 6C:
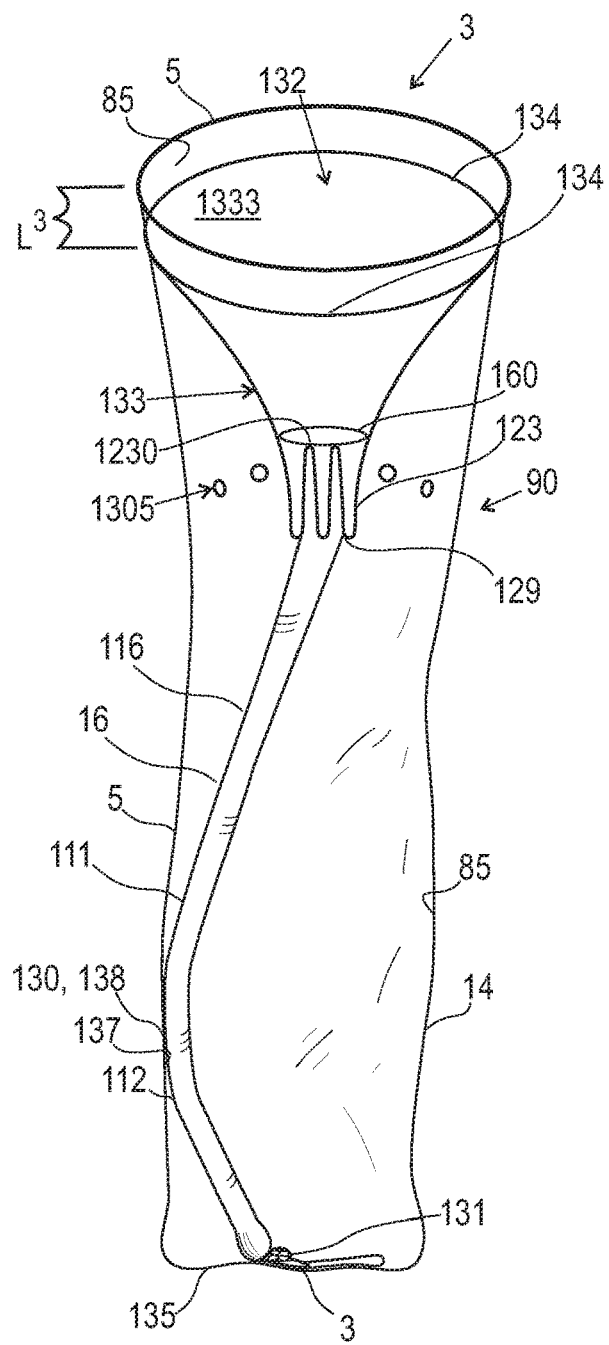
FIG. 6C depicts leak-resistant Kit 3, after insertion of the medical suction tube through the displaceable retaining member, in accordance with embodiments of the present invention.
Figure 10:
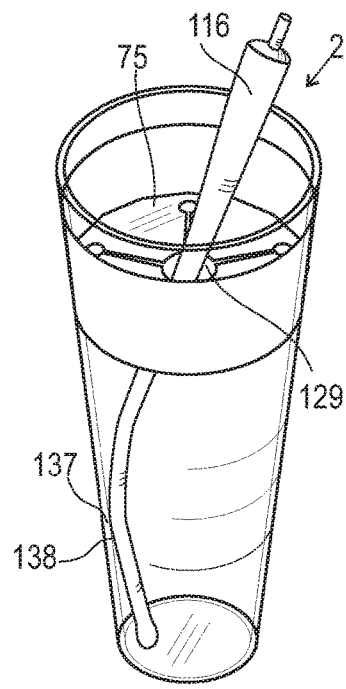
FIG. 10 depicts a front elevation view of the leak-resistant Kits 1, 2, 3, in accordance with embodiments of the present invention.

FIGS. 10 and 6C depict a front elevation view of the leak-resistant Kits 2, 3. Kits 2, 3 are alternative embodiments of Kit 1 depicted in FIGS. 3A-3B in which the retaining disk 75 of Kit 2 is displaceable, represented by $L_2$, and the displaceable retaining member 1333 of Kit 3 is displaceable, represented by $L_3$, instead of the retaining disk 13 being fixed displacement, represented by $L_1$ in Kit 1.

Example 1: Kits 2 and 3 are Improvement Over Kit 1 if Tube 16 in Kit 1 Too Short to Allow Tube 16 to be Propped Up In an illustrative example, the length $L_1$ of a tube 16 in Kit 1 may insufficient to allow the bulbous end 4 at the distal suction end 10 of the tube 16 to reach the bottom end 135 of the retaining holster 5 when the releasable seal 119 in Kit 1 (using a fixed displacement retaining disk 13) has been formed. Therefore the tube 16 can not be supported by resting the bulbous tip 4 on the bottom end 135 of the retaining holster 5 because the tube 16 is not long enough.

The displaceable retaining disk 75 of Kit 2 and the displaceable retaining member 1333 of Kit 3 being displaceable are an improvement over the fixed displacement retaining disk 13 being fixed. In this example, taper (change in diameter/length of tube 16 of Kit 2 or diameter/length of tube 16 of Kit 3) or length of the tube 16 may necessitate the ability to adjust $L_2$ of Kit 2 and $L_3$ of Kit 3 such that the releasable seals 129 may be formed while the tube 16 is propped up. In addition the retaining disk 75 of Kit 2 and the displaceable retaining member 1333 of Kit 3 being displaceable is an improvement in situations where the tube 16 is too short to reach the bottom end 135 of the holster 5 given $L_1$ of the fixed displacement retaining disk 13, which necessitate the ability to adjust $L_2$ and $L_3$ such that the releasable seal 129 may be formed while the tube 16 is propped up.

FIG. 6C depicts a front elevation view of the leak-resistant Kit 3, having been constructed such that the displaceable retaining member 1333 has variable displacement, designated by $L_3$, resistance to displacement of the grippers 123 when the medical suction instrument 16 is inserted in the central aperture 1230 of the displaceable retaining member 1333, point of contact 137 of curved portion 130 of the tube 16 with contact 138 of the inner wall 85 of the retaining holster 5 and the contact of the bulbous tip 4 with the bottom end 135 of the retaining holster 5 exert frictional forces on the tube 16, such that it is propped up by these frictional forces exerted on the tube 16. Said propping up of the tube 16 results in increased stabilization of the medical suction tube 16, e.g., the Yankauer Suction Instrument during storage, releasably holding, releasably retaining, or releasably restricting from undesired movement.

In addition, leak-resistant Kit 3 may have improved stability because $L_3$ of the displaceable retaining member 1330 may be increased so that the medical suction tube 16 may be propped up.

FIGS. 1, 3A-3B, 6C, 9, 10, 11, 13 and 14 show that a portion of the medical suction tube 16, e.g., Yankauer Suction Instrument forms a curved portion 130 approximately 50% along its length. The curved portion 130 allows for increased stabilization of the medical suction tube 16, e.g., the Yankauer Suction Instrument during storage, releasably holding, releasably retaining, or releasably restricting from undesired movement because the outer surface 138 of the tube 16 may be propped up.

Technical Problem:

In common practice today, a medical suction tube 16, e.g., Yankauer Suction Instrument may be placed in various locations so that it is readily available at a moments notice. Some of these locations include: under a patient's pillow, between the mattress and bed frame, or slung over nearby medical equipment, for example, an anesthesia machine, a work cart, IV pole, etc. In many cases, a medical suction tube 16, e.g., a Yankauer Suction Instrument and/or its original package 18 may fall to the floor. Although a medical suction tube 16, e.g., a Yankauer Suction Instrument is intended for single patient use, it often is used more than once for that same single patient, even though the medical suction tube 16, e.g., Yankauer Suction Instrument may have been contaminated by germs in its surroundings or environment.

Prior to a medical procedure being performed, there is a mandatory check that obligates medical personnel to manually validate that the suction system is working properly. Next, referring to FIG. 1, coupling 8 at the proximal end 7 of the medical suction tube 16, e.g., Yankauer Suction Instrument may be accessed by opening the end 6 of the sterile package 18 and coupled to the suction tubing 17 at one of the ends 12 and typically remains coupled throughout the entire medical procedure. Nearly all users keep the suction end that is the distal suction end 10 of a medical suction tube 16, e.g., a Yankauer Suction Instrument, i.e., in the original packaging even after the protective package 18 is opened in an attempt to make use of the original packaging as a protective covering. However, once the package 18 is opened, the package is unable to protect a medical suction tube 16, e.g., a Yankauer Suction Instrument from contamination from the environment. There is a need to minimize exposure of a medical suction tube 16, e.g., a Yankauer Suction Instrument to environmental contamination after the protective package has been opened. Furthermore, after it has been used to suction the patient's secretions or bodily fluids, many users may still attempt to use the original packaging to serve as a protective covering. This likely may be a serious infection control issue for healthcare workers and patients and may contribute significantly to the high numbers of healthcare acquired infections (HAI).

According to the National Health Service (NHS), bacteria and viruses can live outside of the body. Statistics for the NHS include:
Cold viruses have been shown to survive on indoor surfaces for more than seven days.
Flu viruses can survive on hard surfaces for 24 hours.
Stomach bugs caused by germs such as *Clostridium difficile* (*C difficile*) have been shown to survive for five months on hard surfaces.
Methicillin-Resistant *Staphylococcus Aureus* (MRSA) infections can survive for days to weeks on surfaces.
Norovirus can survive for days to weeks on hard surfaces.
Herpes viruses from cold sores around the mouth can survive for four hours on plastic, three hours on cloth, and two hours on the skin.

According to the Centers for Disease Control and Prevention (CDC), the Hepatitis C virus can survive outside the body at room temperature, on environmental surfaces, for up to three weeks.

According the World Health Organization (WHO), health care-associated infections, or "nosocomial" infections are those acquired by patients in the hospital or facility that are not present or incubating at the time of admission. The WHO states that health care-associated infections are the most frequent adverse event in health-care delivery worldwide. Every year in the U.S., 2 million patients contract infections in hospitals leading to significant mortality and financial losses for health systems. They estimate that such infections account for 100,000 deaths and costs $30.5 billion dollars in the U.S. annually.

Related art and commercially available options fail to provide a practical solution to the problem of where to place a suction tube, like a medical suction tube 16, e.g., Yankauer Suction Instrument, to ensure that it and its surroundings remain aseptic and not contaminated. Currently, there exists no holster product capable of reliably retaining a suction tube, so that it can be stored and used for repeated use on a single patient while reducing the environmental spread of contaminants. Also, no holsters formerly developed offer a one-handed use of a suction tube. In addition, there are no retaining holsters developed for a suction tube that can be easily moved with one hand and placed on multiple surfaces and orientations whether round, square, rectangle, horizontal, or vertical, giving a medical or dental provider the added benefit of having the suction tube, such as a medical suction tube 16, e.g., Yankauer Suction Instrument, exactly where they need it, and when they need it. Also, there is a need for leak-resistant containment of any biological fluids 3 that might be present on the medical suction tube, 16, during use and after use in a medical procedure.

Convenience and cost are critical factors that determine how and when medical equipment is used in common, everyday medical practice. A medical suction tube 16, e.g., Yankauer Suction Instrument may be individually wrapped in a sterile package. Currently, most providers attempt to use this original package as its protective covering. This invention will allow the user the option to place a medical suction tube 16, e.g., Yankauer Suction Instrument with its package inside the retaining holster, if desired, but also gives the user the option to discard the package and simply place a medical suction tube 16, e.g., Yankauer Suction Instrument inside the disposable leak-resistant retaining holster 5.

The invention disclosed herein is an improvement on existing methods and devices that serve to hold suction tubes, such as a medical suction tube 16, e.g., Yankauer Suction Instrument, for access during medical and dental procedures. It includes a variety of mounting means depending on the exact environment that it is to be used in, and a containment device structure that provides aseptic control by retaining a medical suction tube 16, e.g., Yankauer Suction Instrument, and specifically functions to allow for a one-handed operation to optimize user access and patient safety. The invention disclosure also contemplates offering the containment device independently or as a kit, comprising the suction tube containment device, and/or one or more attachment means for various placement in the medical or dental patient care environment. This invention also contemplates that the retaining holster be of a disposable nature while the mounting means be of a non-disposable nature. In certain circumstances, the retaining holster could be made non-disposable yet cleanable if desired by the user.

FIGS. 3A-3B, 4, and 5 depict front elevation views of a Kit 1, comprising a retaining holster 5 and a medical suction tube 16, e.g., a Yankaurer Suction Instrument. The leak-resistant retaining holster 5 of Kit 1, comprising a rim end 15, a leak-proof opposing bottom end 135, with a reservoir 14 between them for containing drippings 131 of biological fluids 3 from the medical suction tube 16, e.g., Yankauer Suction Instrument, and a recessed lid 50. The recessed lid 50 comprises a coupling 110 and a recessed portion 109, extending from an overlapping edge 105 to a distal suction end 9. The overlapping edge 105 overlaps the rim end 15 of the container, such that the rim end 15 fits into groove 1332 formed when rim end 15 and overlapping edge 105 are operably coupled frictionally or threaded to rim 15.

The recessed lid 50 further comprises a fixed displacement retaining disk 13 that is peripherally coupled to a distal suction end 9 of a recessed portion 109, such that there is a measurable length $L_1$ separating the rim end 15 from a top surface 40 of the fixed displacement retaining disk 13. The fixed displacement retaining disk 13 has slits 23 that radiate from a center 60, where the slits 23 divide the fixed displacement retaining disk 13 into a plurality of flexible arcuate flaps 65. At least one of the plurality of flexible arcuate flaps 65 flex toward the bottom end 135 when the suction end 10 of the suction tube 16 contacts the plurality of flexible arcuate flaps 65 during insertion of said suction end 10 of the suction tube 16 into the hollow cavity 132. This forms a central aperture 70 through the center 60 of the recessed lid 50. The flexible arcuate flaps 65 and central aperture 70 of the recessed lid are thus operative in combination with said suction tube 16 as a splash guard 133 for preventing biological fluids 3 from being ejected from a reservoir 14 of the hollow cavity 132 between the recessed lid 50 and the bottom end 135, and for releasably retaining the suction end 10 of the suction tube 16 in the reservoir 14 after insertion of the suction end 10 through the central aperture 70.

The recess 109 of the recessed lid 50 is defined by the vertical length $L_1$ separating the overlapping extension 105 from the top surface 40 of the fixed displacement retaining disk 13. $L_1$ may advantageously be from 0.1 to 6 in. Alternatively $L_1$ may be 2 in. to 4 in. Alternatively $L_1$ may be 3 in. to 6 in. Alternatively $L_1$ may be 0.4 to 0.6 in. Alternatively $L_1$ may be 0.5 in.

An internal portion 45 of the top surface 40 forms a fixed displacement retaining disk 13, and a peripheral portion 55 of the top surface 40 overlaps the rim end 15 of the leak-resistant holster 5, such that the fixed displacement retaining disk 13 is secured or anchored by overlapping or snapping onto the rim end 15. The recessed lid 50 has slits 23 that radiate from a center 60 of the recessed lid 50. The slits 23 divide the recessed lid 50 into a plurality of flexible arcuate flaps 65. At least one of the plurality of flexible arcuate flaps 65 flex toward the bottom end 135 when the suction end 10 of the suction tube 16, e.g., Yankauer Suction Instrument contacts the plurality of flexible arcuate flaps 65 during insertion of the suction end 10 of the suction tube 16 into the hollow cavity 132, forming a central aperture 70 through the center 60 of the recessed lid 50. The flexible arcuate flaps 65 and central aperture 70 of the recessed lid 50 are operative in combination with the suction tube 16 as a splash guard 133 and for releasably retaining said suction end 10 of the suction tube 16 in the reservoir 14 after insertion of said suction end 10 through the central aperture 70.

The leak resistant Kits 1, 2, 3 may contain a feature where the outer wall 136 of the holster 5 includes a fastener 20 for releasably coupling the holster 5 to a holding station 35 before use, during use, or after use of the medical suction tube 16.

FIGS. 7, 8, 9, and 10 depict a second aspect of the present invention. The second aspect of the present invention provides a leak-resistant kit 2 for releasably retaining a medical suction tube 16, e.g., a Yankauer Suction Instrument before use, during use, or after use to collect biological fluids 3 during a medical procedure. The leak-resistant kit 2 contains a holster 5 having a rim end 15 and an opposing leak-proof bottom end 135. Only the rim end 15 is open, and opens into a hollow cavity 132. The kit 2 also contains a displaceable retaining disk 75 having a central aperture 70 in a top surface 240 for insertion of the suction end 10 of a medical suction tube 16, e.g., a Yankaurer Suction Instrument into the hollow cavity 132. The displaceable retaining disk 75 has slits 23 that radiate from a center 60, the slits 23 dividing the retaining disk 75 into a plurality of flexible arcuate flaps 65. At least one of the plurality of flexible arcuate flaps 65 flexes towards the bottom end 135 when the suction end 10 of the suction tube 16 contacts the plurality of flexible arcuate flaps 65 during insertion of the suction end 10 of the suction tube 16, e.g., a Yankauer Suction Instrument into the hollow cavity 132. This forms a central aperture 70 through the center 60 of the displaceable retaining disk 75. The flexible arcuate flaps 65 and central aperture 70 of the displaceable retaining disk 75 are operative in combination with the suction tube 16 as a splash guard 133 for preventing biological fluids 3 from being ejected from the reservoir 14 of the hollow cavity 132 that is between the displaceable retaining disk 75 and the bottom end 135 and for releasably retaining the suction end 10 of the suction tube 16 in the reservoir 14 after insertion of the suction end 10 through the central aperture 70.

Figure 7:
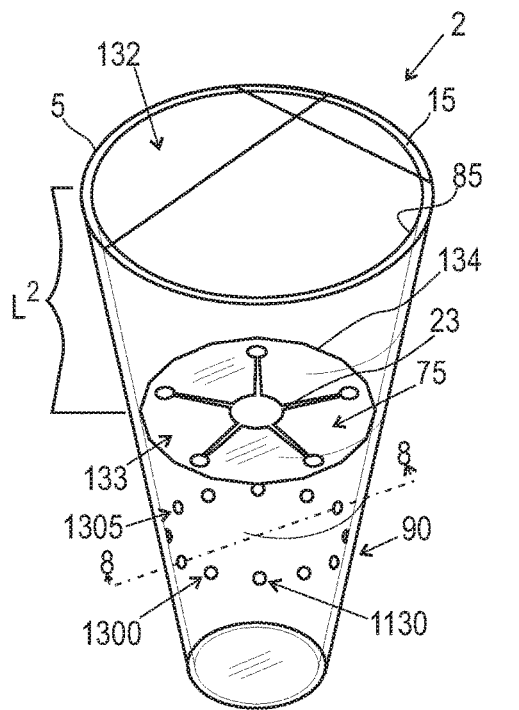
FIG. 7 depicts a front elevation view of the leak-resistant Kit 2, after opposing Light Emitting Diode (LED) arrays have been arranged circumferentially along the inner wall of the retaining holster, in accordance with embodiments of the present invention.

FIG. 7 shows the displaceable retaining disk 75 may be displaced lengthwise along the holster 5 as represented by $L_2$ that is defined as a length separating rim end 15 from a top surface 240 of the displaceable retaining disk 75. $L_2$ may advantageously be from 0.1 to 6 in. Alternatively $L_2$ may be 2 in. to 4 in. Alternatively $L_2$ may be 3 in. to 6 in. Alternatively $L_2$ may be 0.4 to 0.6 in. Alternatively $L_2$ may be 0.5 in.

Any one of the aforementioned leak-resistant Kits 1, 2, 3 may have the outer wall 136 of the holster 5 include a fastener 20 for releasably coupling the leak-resistant Kits 1, 2, 3 to a holding station 35 before use, during use, or after use of the medical suction tube 16, e.g., a Yankauer Suction Instrument.

The retaining disks 13, 75, or displaceable retaining member 1333 of the aforementioned leak-resistant Kits 1, 2, 3, respectively, may be made from a water proof material selected from the group consisting of elastomeric plastic, elastomeric silicone, and rubber.

FIGS. 6B and 7 depict the holster 5 may be equipped with ultra violet (UV) Light Emitting Diode (LED) arrays 90, arranged circumferentially along the inner wall 95 of the holster 5 in adjacent parallel arrays selected from the group consisting of vertical arrays 1370, horizontal arrays 1375, diagonal arrays 1137, and combinations thereof. Therefore the medical suction tube 16, e.g., a Yankauer Suction Instrument inserted into any of the leak-resistant Kits 1, 2, 3 may be radiated with ultra violet (UV) light from the Light Emitting Diode (LED) arrays 90 because Kits 1, 2, 3 may comprise the retaining holster 5 depicted in FIGS. 6B and 7.

A third aspect of the present invention provides a method of releasably retaining a medical suction tube 16, e.g., a Yankaurer Suction Instrument after being used to collect biological fluids 3 during a medical procedure. The method consists of: providing any one of leak-resistant Kits 1, 2, or 3 for retaining said suction tube 16 after insertion of the suction end 10 of the suction tube 16 through the central aperture 70, 1230 and then releasably inserting the medical suction tube 16 into the central aperture 70, 1230.

Any of the leak-resistant Kits 1, 2, 3 may include a fastener 20 for operably coupling the holster 5 to the holding station 35 before use, during use, or after use of the medical suction tube 16. The fastener 20 may be selected from the group consisting of a tongue in groove fastener 104 and a spring clamp fastener 120.

The reservoir 14 may be of a cylindrical shape. Alternatively the reservoir 14 may be frustoconical, oval. or cube shaped. One skilled in the art would appreciate that alternative shapes capable of supporting the medical suction tube 16 while keeping it at least partially enclosed and retained within the holster would be included in this disclosure. The reservoir 14 may be made out of a plastic type material, durable enough to withstand normal usage without breakage. Other contemplated materials include, rubber, silicone, vinyl, or metal.

Figure 5:
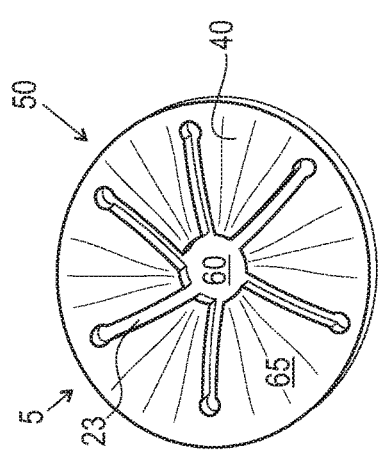
FIG. 5 depicts a cross sectional view of the retaining disk used in leak-resistant Kits 1, 2, 3, taken along the line 5-5 of FIG. 4, in accordance with embodiments of the present invention.

FIGS. 6A-6C depict front elevation views of an alternative embodiment of the retaining holster 5 of FIGS. 1-5, and 7-15 advantageously having a displaceable retaining member 1333 in which elongated grippers 123 extend coaxially about a central aperture 1230, forming an annulus 160. The annulus 160 formed by the elongated grippers 123 of the displaceable retaining member 1333 has a diameter less than any diameter of the medical suction tube 16, e.g., Yankauer Suction Instrument along its entire length, such that the coaxial elongated grippers 123 function to releasably hold, or releasably retain the medical suction tube 16, squeeze or otherwise narrow the aperture of the annulus 160 in order to hold or retain the medical suction tube 16 in place inside the reservoir 14, yet to provide a wide enough opening to allow for the placement and removal of the medical suction tube 16, in and out, as many times as is needed with the simple force of a human user's hand 19.

FIG. 6C shows the displaceable retaining member 1333 may be displaced lengthwise along the holster 5 as represented by $L_3$ that is defined as a length separating rim end 15 from a top surface 340 of the displaceable retaining member 1333. $L_3$ may advantageously be from 0.1 to 6 in. Alternatively $L_3$ may be 2 in. to 4 in. Alternatively $L_3$ may be 3 in. to 6 in. Alternatively $L_3$ may be 0.4 to 0.6 in. Alternatively $L_3$ may be 0.5 in.

Figure 14:
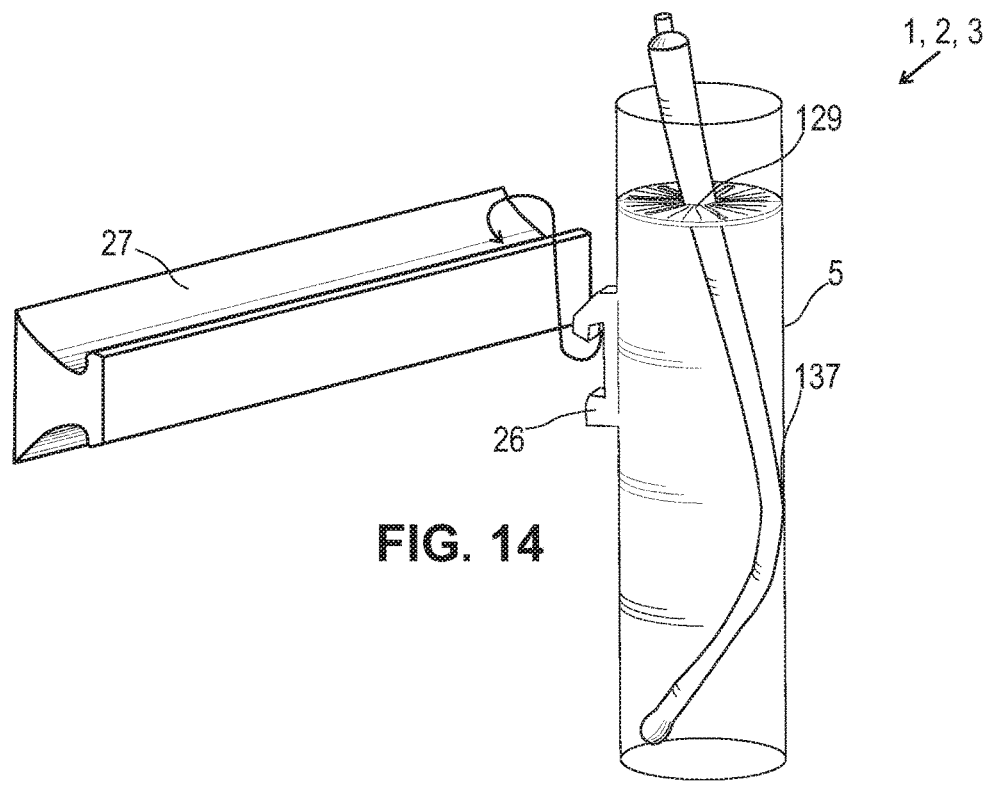
FIGS. 14-15 depict side elevation views of the leak-resistant Kits 1, 2, or 3, after being operably coupled to a retaining holster wall bracket 27, in accordance with embodiments of the present invention.
Figure 15:
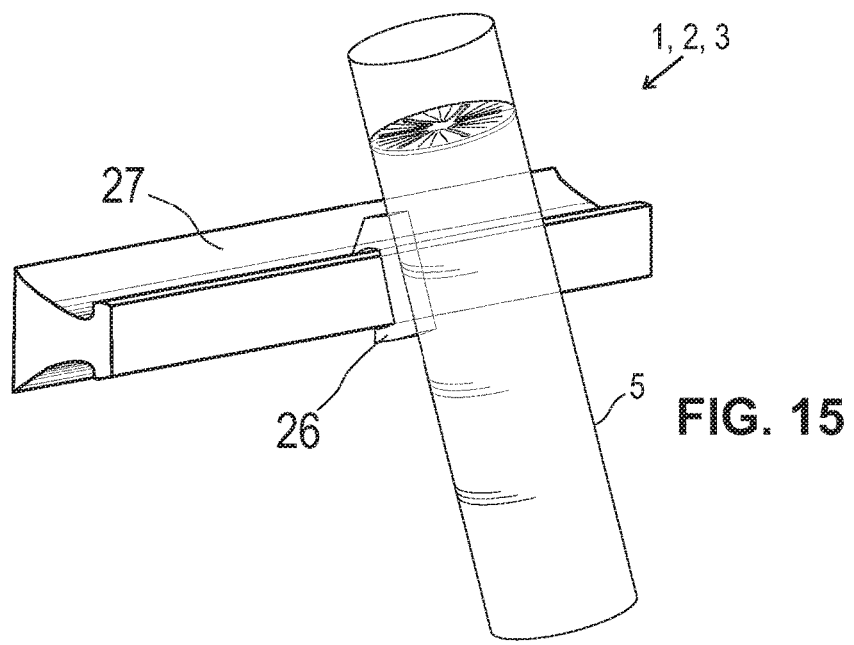

FIGS. 14-15 depict the retaining holster 5 may be clamped in a location convenient for its use using a fastener 20 that can be operated with one hand and can attach to many types of surfaces, whether round, square, rectangle, or horizontal or vertical in orientation. Fastener 20 may include, but is not limited to one or more of the following: a spring clamp fastener 120, a tongue in groove fastener 104, a quick grip clamp, a bar clamp, or a handy clamp, are contemplated. A further embodiment for this feature incorporates a flexible or fixed positioning arm 21, 24 to hold the Kits 1, 2, 3 in place. Another means of attachment will be of a retaining holster wall bracket mount 26 so that the reservoir 14 can be attached to a wall bracket 27. Multiple embodiments of various attachment means 20 and 26 are contemplated herein so as to provide versatility for a variety of environments and for the ease of use of the medical suction tube 16 with one hand 19, without the need to us another hand to hold the retaining holster 5 in the convenient position.

FIG. 2 is a perspective side of a typical suction tubing 17 with both ends 12 being of the same configuration, so that either end can connect to the distal suction end of the medical suction tube 16, e.g., a Yankauer Suction Instrument.

The retaining holster 5 and retaining disk 13, 75, and displaceable retaining member 1333 of the Kits 1, 2, 3 may be made of a material selected from the following materials: rubber, but may also be made of plastic, silicone, paper, or a polymeric material. It will preferably be made as a solid construction and will have cut out slits 23, openings, slits, or teeth-like projections 123 such as to allow the medical suction tube 16, e.g., a Yankauer Suction Instrument to be removed or replaced as many times as needed with ease by a single human hand 19, yet retained inside the reservoir 14 when not in use. It is also contemplated that if the user desires to use the medical suction tube 16, e.g., a Yankauer Suction Instrument's original sterile package 18, it can easily be placed with the medical suction tube 16 inside it, into the reservoir 14 of the retaining holster 5.

FIG. 5 is a cross-sectional view of the fixed displacement retaining disk 13.

FIG. 7 is a side elevation view of the retaining holster 5 having a reservoir 14, a fixed displacement retaining disk 13 affixed inside the wall 85 of the reservoir 14 of the retaining holster 5.

Figure 8:
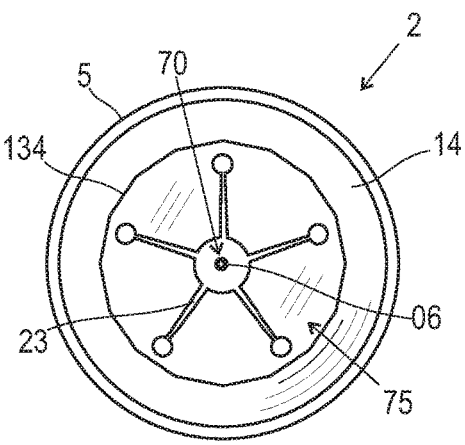
FIG. 8 depicts a cross sectional view of the Kit 2, taken along the line 8-8 of FIG. 7, in accordance with embodiments of the present invention.

FIG. 8 is a perspective top view of the inside of the holster body 14 with a top view of a fixed displacement retaining disk 13.

Figure 9:
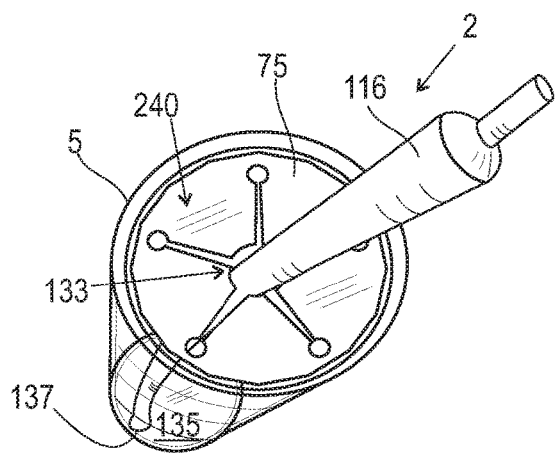
FIG. 9 depicts a top elevation view of the leak-resistant Kit 2, in accordance with embodiments of the present invention.

FIG. 9 is a perspective top view of a medical suction tube 16, e.g., a Yankaurer Suction Instrument inside and through the fixed displacement retaining disk 13, inside the reservoir 14. of the retaining holster 5.

FIG. 10 is a perspective side view of a medical suction tube 16, e.g., a Yankaurer Suction Instrument inside and through the fixed displacement retaining disk 13, inside the holster body 14.

Figures 11, 12:
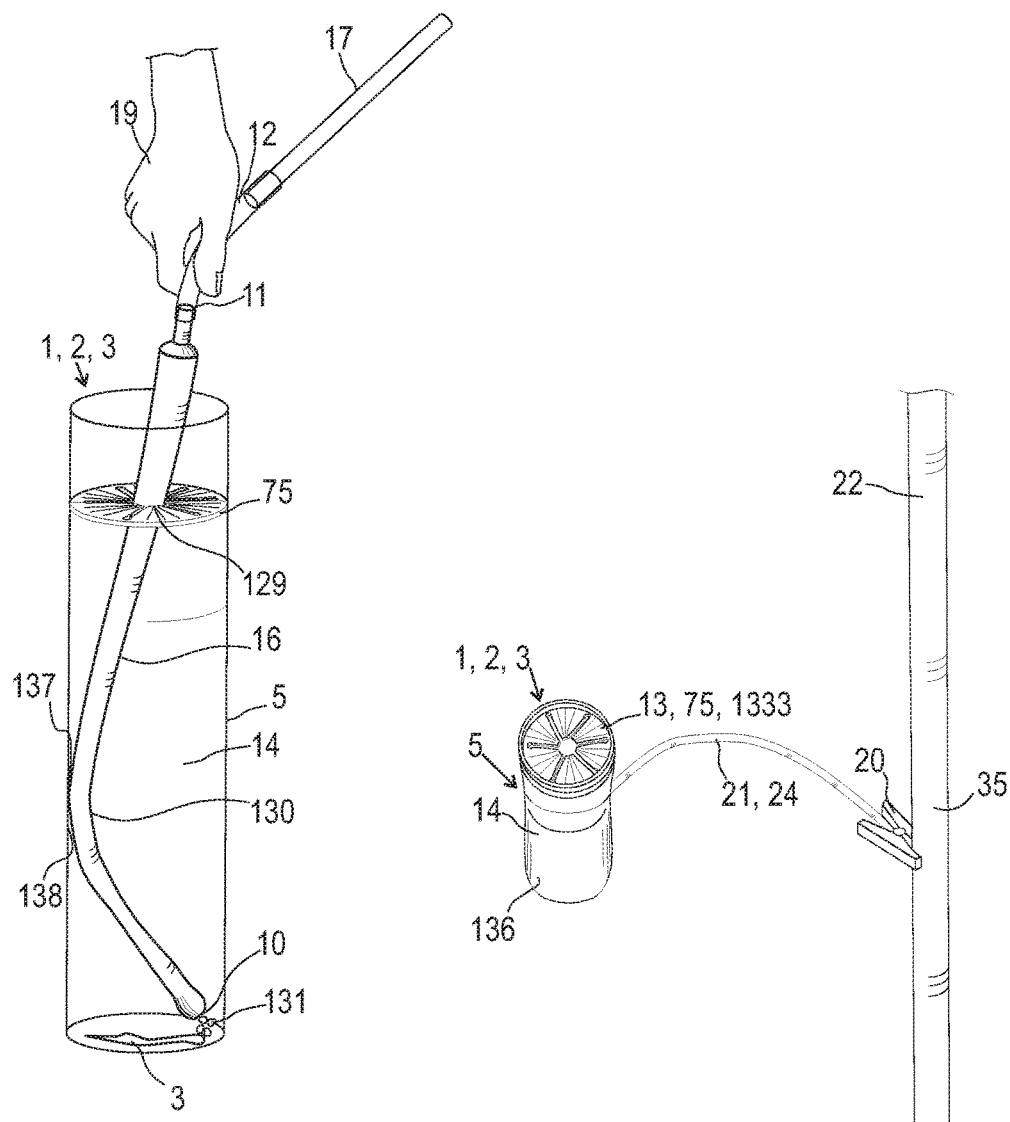
FIG. 11 depicts a front elevation view of leak-resistant Kits 1, 2, 3, including a human hand 19 holding a medical suction tube 16, e.g., a Yankauer Suction Instrument to remove or replace the tube out of or into a retaining holster 5, in accordance with embodiments of the present invention.
FIG. 12 depicts a side elevation view of leak-resistant Kits 1, 2, 3, including a retaining holster attached to a typical round pole via a clamp 20 with a fixed positioning arm 21 or flexible positioning arm 24 connected to the retaining holster, in accordance with embodiments of the present invention.

FIGS. 11-12 are perspective side views of the Kits 1, 2, 3, depicting a user's hand 19 holding the manipulating end of a Yankauer 11, connected to a suction tubing 17. This view shows the medical suction tube 16, e.g., a Yankaurer Suction Instrument inside the reservoir 14 of the leak-resistant Kits 1, 2, 3 and through the opening of the retaining disks 13, 75, or displaceable retaining member 1333.

Referring to FIG. 12, the Kits 1, 2, 3, a flexible or fixed positioning arm 21, 24, respectively, operably couples fastener 20 to a round pole 22. The retaining holster 5 may be clamped in a location convenient for its use using a fastener 20 that can be operated with one hand and can attach to many types of surfaces, whether round, square, rectangle, or horizontal or vertical in orientation. Fastener 20 may include, but is not limited to one or more of the following: a spring clamp fastener 120, a tongue in groove fastener 104, a quick grip clamp, a bar clamp, or a handy clamp are contemplated. A further embodiment for this feature incorporates a flexible or fixed positioning arm 21, 24, respectively, to hold the leak-resistant Kit 1, 2, 3 in place. Multiple embodiments of various attachment means 20 and 26 are contemplated herein so as to provide versatility for a variety of environments and for the ease of use of the medical suction tube 16 with one hand 19, without the need to use another hand to hold the retaining holster 5 in the convenient position.

Figure 13:
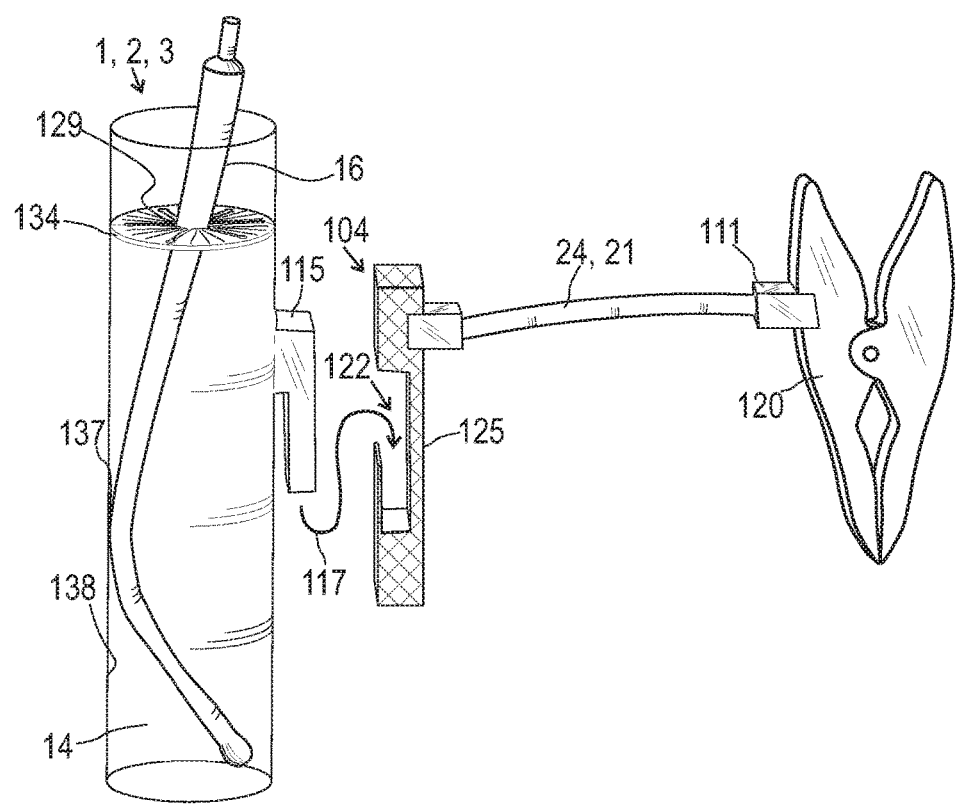
FIG. 13 depicts a side elevation view of leak-resistant Kits 1, 2, 3, including a retaining holster with a medical suction tube, e.g., a Yankauer Suction Instrument inside, showing the holster operably coupled to a tongue and groove fastener, in accordance with embodiments of the present invention.

FIG. 13 is a perspective side view of the retaining holster 5 of Kits 1, 2, 3 operably coupled to a round pole 22 using a retaining holster bracket mount 25, a flexible positioning arm 21 or fixed positioning arm 24 and fastener 20.

FIGS. 14 and 15 are perspective side views of view of the retaining holster 5 of Kits 1, 2, 3, being operably coupled to a retaining holster wall bracket mount 26. This view shows how the retaining holster wall bracket mount 26 would connect to a wall bracket 27.

Figure 16:
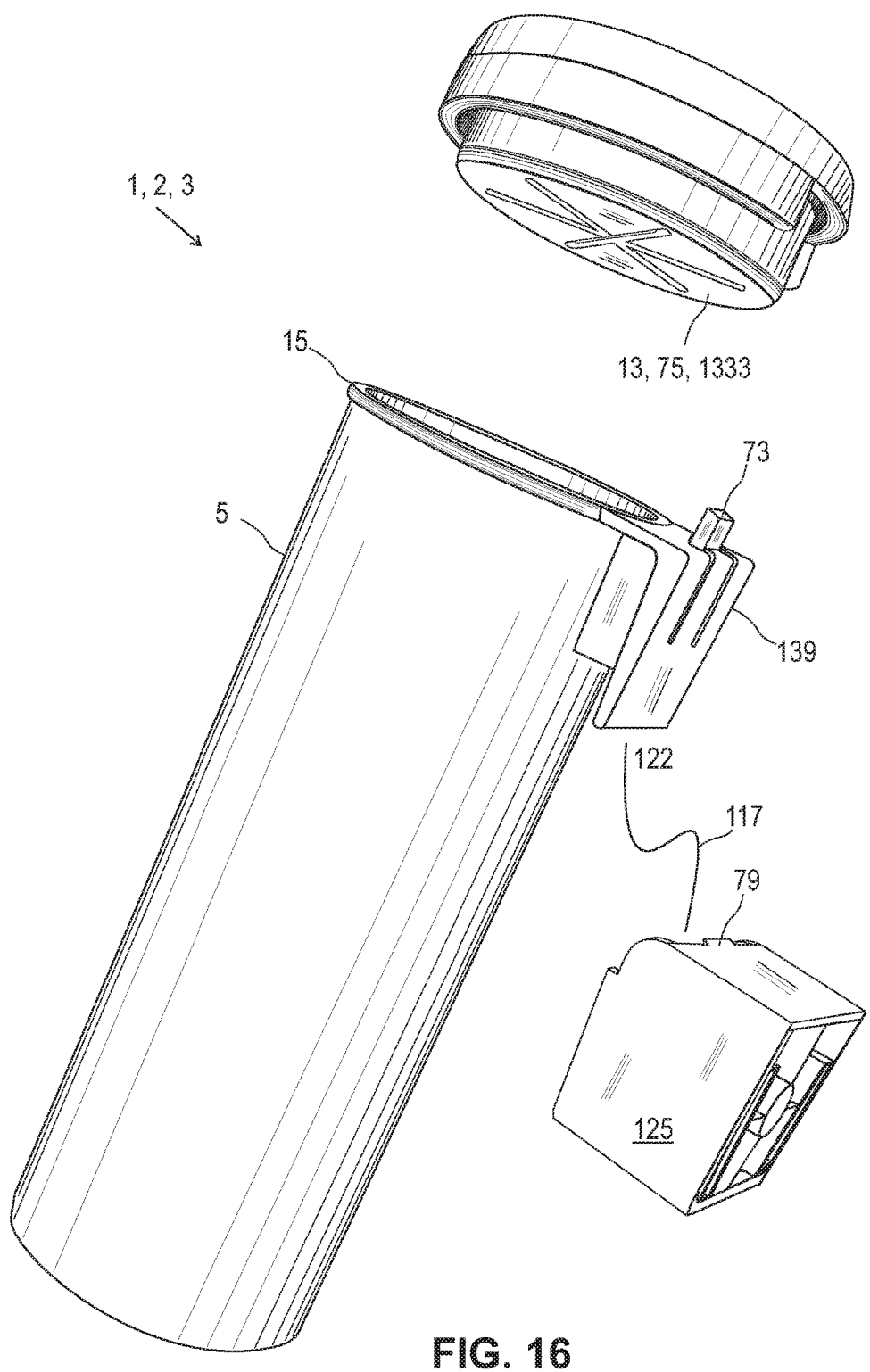
FIG. 16 depicts a side elevation view of the leak-resistant Kits 1, 2, or 3, after being operably coupled to a tongue in groove fastener 104, in accordance with embodiments of the present invention.

FIG. 16 depicts a side elevation view of the leak-resistant Kits 1, 2, or 3, after being operably coupled to tongue in groove fastener 104, including a tongue 139 and a mounting bracket 125, for operably coupling the retaining holster 5 to a wall or other appropriate structural support in a hospital room (not shown). The tongue 139 may be inserted into a groove 122 of the mounting bracket 125 by aligning the tongue 139 with the groove 122, then inserting the tongue 139 in the direction of the arrow 117. The tongue 139 may be locked in place after insertion into the groove 122. Pin 73 is forced past blocking pin 79 during insertion, causing non-alignment of the tongue with the groove until the pin 73 travels past the blocking pin 79. The tongue 139 is prevented from sliding out of the groove 122 because the blocking pin 79 acts as a obstacle, preventing pin 73 and the tongue 139 from going in the opposite direction of the arrow 117.

Figure 17:
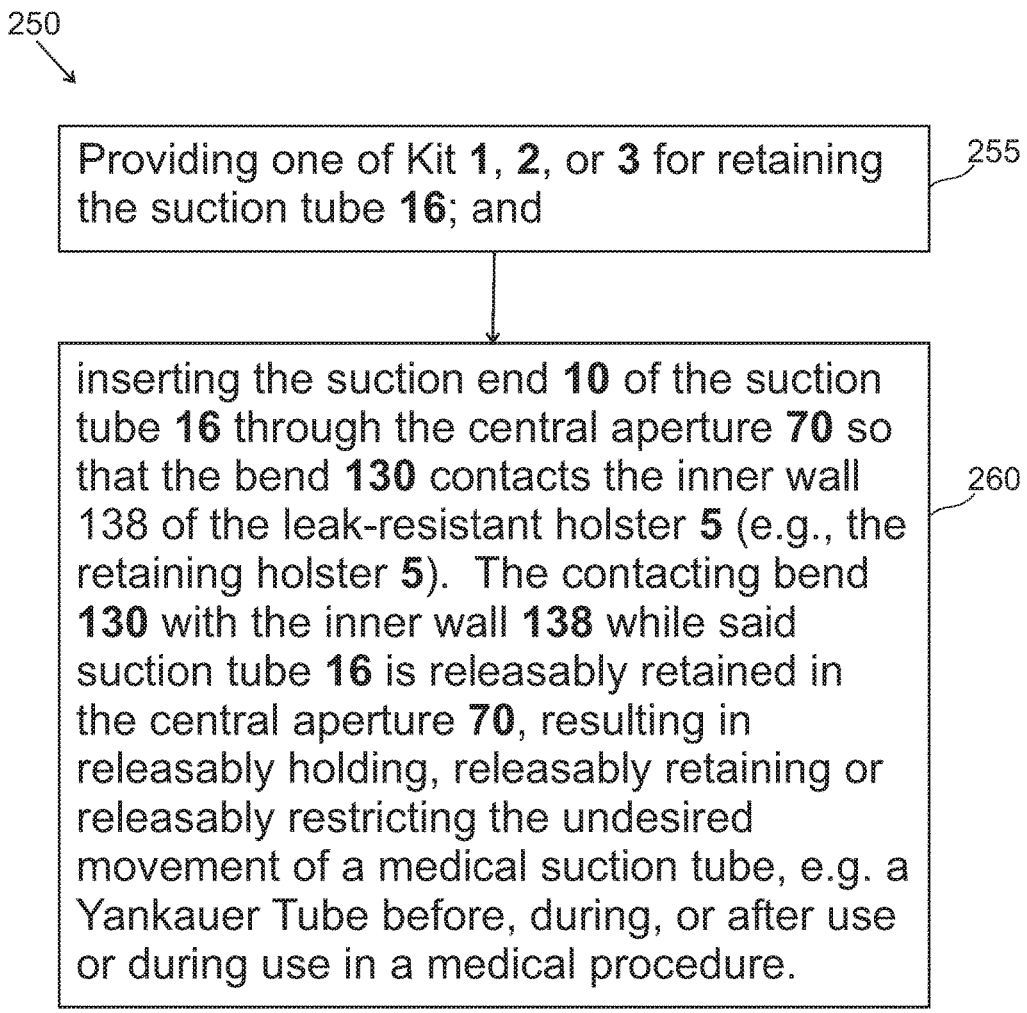
FIG. 17 depicts a flow diagram for a method 250 of releasably holding, releasably retaining or releasably restricting the undesired movement of a medical suction tube, e.g. a Yankauer Tube before, during, or after use or during use in a medical procedure, in accordance with embodiments of the present invention.

FIG. 17 depicts a flow diagram for a method 250 of releasably holding, releasably retaining or releasably restricting the undesired movement of a medical suction tube, e.g. a Yankauer Tube before, during, or after use or during use in a medical procedure.

Figure 18:
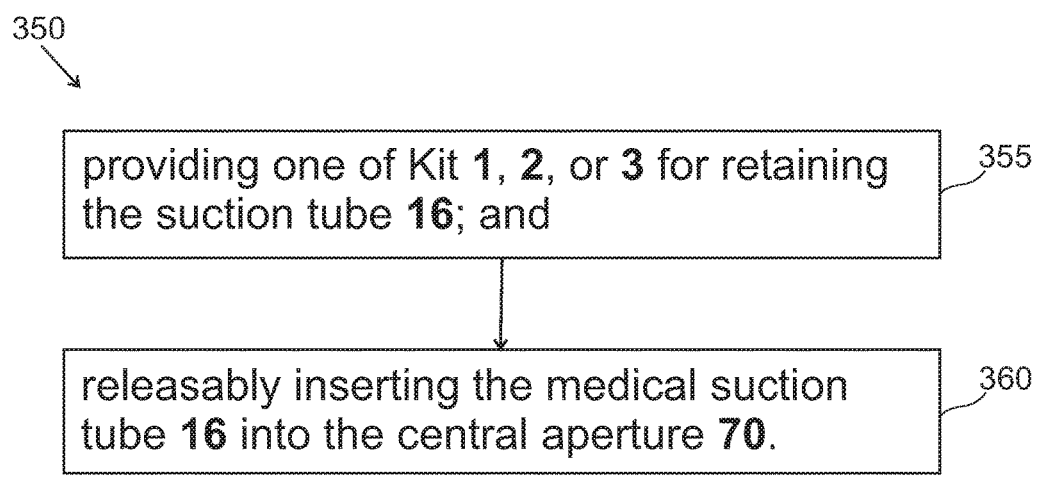
FIG. 18 depicts a flow diagram of a method 350 for releasably retaining the medical suction tube 16 after being used to collect biological fluids 3 during a medical procedure, in accordance with embodiments of the present invention.

FIG. 18 depicts a flow diagram of a method 350 for releasably retaining the medical suction tube 16 after being used to collect biological fluids 3 during a medical procedure.

Figure 19:
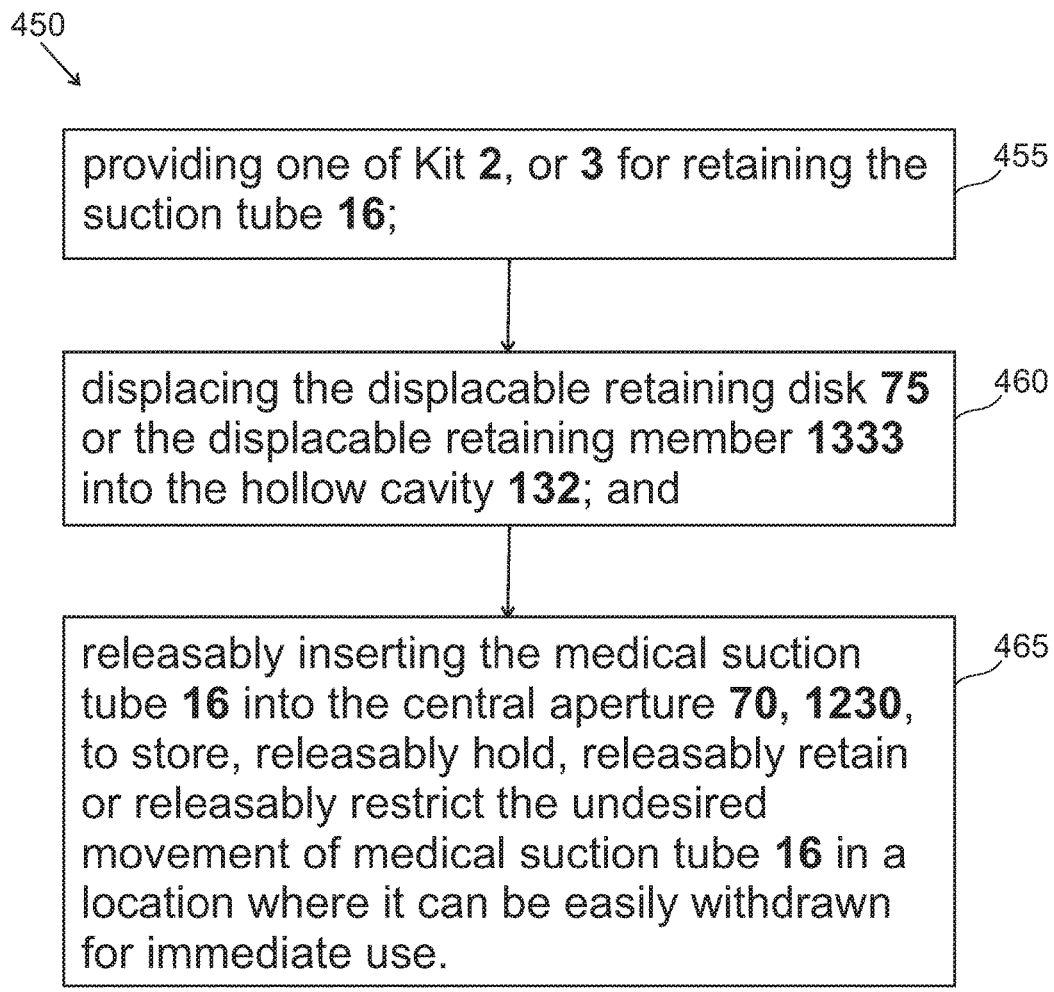
FIG. 19 depicts a flow diagram of a method 450 for releasably retaining the medical suction tube 16 after being used to collect biological fluids 3 during a medical procedure, in accordance with embodiments of the present invention.

FIG. 19 depicts a flow diagram of a method 450 for releasably retaining the medical suction tube 16 after being used to collect biological fluids 3 during a medical procedure.

FIG. 20 depicts a flow diagram of a method 550 for positioning the fixed displacement retaining disk 13 or the displaceable retaining disk 75 or the displaceable retaining member 1333 along a length L1, L2, or L3 of the hollow cavity 132

EXAMPLE 1

METHOD OF OPERATION

The set up for using a Yankauer Suction Instrument begins with a mandatory check of the suction system, which consists of opening the original, sterile package of the Yankauer Suction Instrument at the peel apart end and connecting it to one end of the suction tubing. The other end of the suction tubing is connected to a suction collection canister which houses a regulator to operate the suction system. Upon connection, the user manually checks the suction operation. Once the suction system has been verified to be working properly, the Yankauer Suction Instrument, still connected to the suction system is simply through the central aperture 70 of the retaining disk 13, 75 of Kits 1, 2 or central aperture 1230 of the displaceable retaining member 1333 of Kit 3 where it remains until needed for use.

When the medical provider needs to use a medical suction tube 16, e.g., Yankauer Suction Instrument for treating a patient, he/she simply grasps the medical suction tube 16, e.g., the Yankauer Suction Instrument of the present invention with one hand, and pulls it out of the retaining holster. If the user desires to use the original sterile package 18 that the Yankauer Suction Instrument comes with, he/she simply places the Yankauer Suction Instrument inside the package through the fixed displacement retaining disk 13, into the reservoir 14 of the retaining holster 5. When it is needed to be used, the user simply pulls the Yankauer Suction Instrument out and the original package 18 remains inside the reservoir 14 of the retaining holster 5. This option is not necessary but certainly is a viable option to those users who routinely use the original package 18 as a means of covering for the Yankauer Suction Instrument once opened, and don't want to break that habit. Either way, the Yankauer Suction Instrument can be withdrawn and replaced inside the reservoir 14 of the retaining holster 5 as many times as necessary with one hand 19 for the care of that patient. Once the care of that patient has concluded, the user simply discards the disposable retaining holster 5 along with the medical suction tube 16, e.g., the Yankauer Suction Instrument.

The retaining holster will be constructed with a male type mounting means that will fit into a receiving female type fitting on a mounting bracket 125. The mounting bracket 125 will preferably have a flexible or fixed arm that is attached to a clamp that can easily be manipulated with one hand. The purpose of this is so that the user can easily move the retaining holster with one hand to wherever they need for it to be located in order to best care for their patient. It will be constructed so that the entire apparatus can be moved to various locations and affixed to many types of surfaces that are normally found in medical procedure rooms, ambulances, patients' hospital rooms, operating rooms, emergency rooms, recovery rooms, etc.

This disclosure further describes a kit for providing a retaining holster, support, storage, and method of use for one-handed aseptic operation of a suction tube. One skilled in the art would also appreciate that it could be used with instruments and other devices besides the Yankauer Suction Instrument that would require immediate access in a medical or dental procedure environment and would benefit from a one-handed, aseptic operation.

While exemplary embodiments have been specifically disclosed, it should be understood that the practice of this invention is not limited to those embodiments. Modifications and variations falling within the spirit of the invention will occur to those skilled in the art. Therefore, it is not intended that the scope of the invention be determined by the disclosed exemplary embodiments, but rather should be determined by the breadth of the appended claims.

I claim:

1. A retaining holster (5), comprising:
   a rim end (15);
   a leak-proof opposing bottom end (135);
   a reservoir (14), therebetween, for containing drippings (131) of biological fluids (3) from a suction tube (16),
   wherein the reservoir has a shape selected from the group consisting of a cylinder, a frustroconical shape, an oval shape and a cubic shape; and
   a recessed lid (50), comprising:
      a coupling (110); and
      a recessed portion (109), extending from an overlapping edge (105) of the recessed portion (109) to a distal suction end (9) of the recessed portion (109), wherein the overlapping edge (105) overlaps the rim end (15) of the retaining holster (5), such that the rim end (15) is covered by the overlapping edge (105), resulting in the rim end (15) and the overlapping edge (105) fitting into a groove (1332);
      wherein the recessed portion (109) has a length $L_1$;
   a fixed displacement retaining disk (13), peripherally coupled to the distal suction end (9) of the recessed portion (109), such that $L_1$ determines a length separating rim end (15) from a top surface (40) of the retaining disk (13), comprising:
      slits (23) that radiate from a center (60),
         wherein the slits (23) divide the retaining disk (13) into a plurality of flexible arcuate fenestrated flaps (65), and
      wherein at least one of the plurality of flexible arcuate fenestrated flaps (65) flex toward a bottom end (135) when a suction end (10) of the suction tube (16) contacts the plurality of flexible arcuate fenestrated flaps (65) during insertion of said suction end (10) of the suction tube (16) into a hollow cavity (132), forming a central aperture (70) through the center

(60) of the recessed lid (50), said flexible arcuate fenestrated flaps (65) and central aperture (70) of said recessed lid (50) being operative in combination with said suction tube (16) as a splash guard (133) for preventing the biological fluids (3) from being ejected from a reservoir (14) of the hollow cavity (132) that is between the recessed lid (50) and the bottom end (135) and for releasably retaining said suction end (10) of the suction tube (16) in the reservoir (14) after insertion of said suction end (10) through the central aperture (70), and wherein said shape of the reservoir is maintained when suction is applied to the reservoir before use, during use, and after use of the suction tube (16).

2. The retaining holster (5) of claim 1, wherein an outer wall (136) of the retaining holster (5) includes a fastener (20) for releasably coupling the retaining holster (5) to a holding station (35) before use or during use of the medical suction tube (16).

3. The retaining holster of claim 2,
wherein the fastener (20) for operably coupling the retaining holster(5) to the holding station (35) during use of the medical suction tube (16) is a fastener selected from the group consisting of a tongue in groove fastener (104) and a spring clamp fastener (120).

4. The retaining holster of claim 1, wherein the splash guard (133) is made of a material selected from the group consisting of elastomeric plastic, elastomeric silicone, and rubber.

5. The retaining holster of claim 1,
wherein the suction tube (16) is radiated with UV light from opposing Light Emitting Diode (LED) arrays (90) arranged circumferentially along an inner wall (95) of the reservoir (14) in adjacent parallel arrays selected from the group consisting of vertical arrays (1370), horizontal arrays (1375), diagonal arrays (1137), and combinations thereof.

6. The retaining holster of claim 1, further comprising:
packaging (18) having an open end (6) in communication with the suction end (10) of the suction tube (16);
wherein the packaging is a biological fluids barrier between the suction tube and the reservoir, such that the only way the biological fluids may leave the bag is through the open end (6).

7. A leak-resistant kit (1) for releasably retaining a medical suction tube (16) before being used or after being used to collect biological fluids (3) during a medical procedure, comprising:
a medical suction tube (16);
a retaining holster (5), comprising:
a rim end (15);
a leak-proof opposing bottom end (135);
a reservoir (14), therebetween, for containing drippings (131) of the biological fluids (3) from the suction tube (16),
wherein the reservoir has a shape selected from the group consisting of a cylinder, a frustroconical shape, an oval shape and a cubic shape; and
a recessed lid (50), comprising:

a coupling (110); and
a recessed portion (109), extending from an overlapping edge (105) of the recessed portion (109) to a distal suction end (9) of the recessed portion (109),
wherein the overlapping edge (105) overlaps the rim end (15) of the retaining holster (5), such that the rim end (15) is covered by the overlapping edge (105), resulting in the rim end (15) and the overlapping edge (105) fitting into a groove (1332);
wherein the recessed portion (109) has a length $L_1$;
a fixed displacement retaining disk (13), peripherally coupled to a distal suction end (9) of the recessed portion (109), such that $L_1$ determines a length separating rim end (15) from a top surface (40) of the retaining disk (13), comprising:
slits (23) that radiate from a center (60),
wherein the slits (23) divide the retaining disk (13) into a plurality of flexible arcuate fenestrated flaps (65), and
wherein at least one of the plurality of flexible arcuate flaps (65) flex toward a bottom end (135) when a suction end (10) of the suction tube (16) contacts the plurality of flexible arcuate fenestrated flaps (65) during insertion of said suction end (10) of the suction tube (16) into a hollow cavity (132), forming a central aperture (70) through the center (60) of the recessed lid (50), said flexible arcuate fenestrated flaps (65) and central aperture (70) of said recessed lid (50) being operative in combination with said suction tube (16) as a splash guard (133) for preventing the biological fluids (3) from being ejected from a reservoir (14) of the hollow cavity (132) that is between the recessed lid (50) and the bottom end (135) and for releasably retaining said suction end (10) of the suction tube (16) in the reservoir (14) after insertion of said suction end (10) through the central aperture (70), and wherein said shape of the reservoir is maintained when suction is applied to the reservoir before use, during use, and after use of the suction tube (16).

8. A leak-resistant kit of claim 7, further comprising:
packaging (18) having an open end (6) in communication with the suction end (10) of the suction tube (16);
wherein the packaging is a biological fluids barrier between the suction tube and the reservoir, such that the only way the biological fluids may leave the bag is through the open end (6).

9. A method of releasably retaining a medical suction tube (16) after being used to collect biological fluids (3) during a medical procedure, comprising:
providing the leak-resistant kit of claim 7; and
releasably inserting the medical suction tube (16) into the central aperture.

\* \* \* \* \*